US011903742B2

(12) United States Patent
Shivpure et al.

(10) Patent No.: US 11,903,742 B2
(45) Date of Patent: Feb. 20, 2024

(54) NON-INVASIVE NON-CONTACT SYSTEM AND METHOD FOR MEASURING DYSLIPIDEMIA CONDITION USING THERMAL IMAGING

(71) Applicant: Aarca Research Inc., Orange, CT (US)

(72) Inventors: Sameer Raghuram Shivpure, Maharashtra (IN); Jayanthi Thiruvengadam, Tamil Nadu (IN); Anuhya Choda, Andhra Pradesh (IN); Gayathri Choda, Andhra Pradesh (IN)

(73) Assignee: Aarca Research Inc., Orange, CT (US)

( * ) Notice: Subject to any disclaimer, the term of this patent is extended or adjusted under 35 U.S.C. 154(b) by 102 days.

(21) Appl. No.: 17/291,357

(22) PCT Filed: Oct. 20, 2020

(86) PCT No.: PCT/IB2020/059836
§ 371 (c)(1),
(2) Date: May 5, 2021

(87) PCT Pub. No.: WO2021/084375
PCT Pub. Date: May 6, 2021

(65) Prior Publication Data
US 2022/0304629 A1     Sep. 29, 2022

(30) Foreign Application Priority Data
Oct. 31, 2019  (IN) .............................. 201941044162

(51) Int. Cl.
*G06T 7/11* (2017.01)
*G06V 10/25* (2022.01)
(Continued)

(52) U.S. Cl.
CPC ............ *A61B 5/7275* (2013.01); *A61B 5/015* (2013.01); *A61B 5/02007* (2013.01);
(Continued)

(58) Field of Classification Search
CPC . A61B 5/015; A61B 5/02007; A61B 5/02028; A61B 5/02055; A61B 5/0261;
(Continued)

(56) References Cited

U.S. PATENT DOCUMENTS

2003/0028114 A1* 2/2003 Casscells, III ......... A61B 5/418
                                                                  600/474
2008/0045847 A1* 2/2008 Farag .................. A61B 5/02055
                                                                  600/500

(Continued)

OTHER PUBLICATIONS

S.V Mahesh Kumar, "Non-Invasive Measurement of Cholesterol Levels Using Eye Image Analysis," Oct. 19-20, 2016, vol. 14 CIC 2016 Special Issue International Journal of Computer Science and Information Security (IJCSIS), (CIC 2016), Pondicherry Engineering College, Puducherry, India Oct. 19 & 20, 2016, pp. 33-37.*

(Continued)

*Primary Examiner* — Omar S Ismail
(74) *Attorney, Agent, or Firm* — Morse, Barnes-Brown & Pendleton, P.C.; Martin Z. Zhang

(57) ABSTRACT

System and method for measuring dyslipidemia condition of a subject using thermal imaging is disclosed. The disclosed system and method includes thermal sensors for capturing thermal images and/or videos of a body part; and a processing engine to detect a predefined region of the body part in each frame of the captured images and/or videos. The processing engine segments one or more portions from the predefined region in each frame of the captured images and/or videos to identify a ROI comprising arteries in the segmented portions. Based on the identified region of interest, the engine extracts pixel values, representing biosignals, from each frame of the captured images and/or videos to determine parameters associated with a rate of atherosclerotic, levels of lipids and lipoproteins, and hemodynamic factors of the subject. Further a risk score for the dyslipi-
(Continued)

demia condition based on the determined parameters using computational models is measured.

19 Claims, 6 Drawing Sheets

(51) Int. Cl.
| | |
|---|---|
| G06V 10/44 | (2022.01) |
| G06V 40/16 | (2022.01) |
| A61B 5/0205 | (2006.01) |
| A61B 5/026 | (2006.01) |
| A61B 5/145 | (2006.01) |
| A61B 5/1455 | (2006.01) |
| A61B 5/00 | (2006.01) |
| A61B 5/01 | (2006.01) |
| A61B 5/02 | (2006.01) |
| G06T 7/00 | (2017.01) |

(52) U.S. Cl.
CPC ...... *A61B 5/02028* (2013.01); *A61B 5/02055* (2013.01); *A61B 5/0261* (2013.01); *A61B 5/14546* (2013.01); *A61B 5/14552* (2013.01); *A61B 5/489* (2013.01); *A61B 5/7257* (2013.01); *A61B 5/7267* (2013.01); *G06T 7/0012* (2013.01); *G06T 7/11* (2017.01); *G06V 10/25* (2022.01); *G06V 10/443* (2022.01); *G06V 40/171* (2022.01); *G06T 2207/10016* (2013.01); *G06T 2207/10048* (2013.01); *G06T 2207/20056* (2013.01); *G06T 2207/30104* (2013.01); *G06T 2207/30201* (2013.01); *G06V 2201/03* (2022.01)

(58) Field of Classification Search
CPC . A61B 5/14546; A61B 5/14552; A61B 5/489; A61B 5/7257; A61B 5/7267; A61B 5/7275; G06T 2207/10016; G06T 2207/10048; G06T 2207/20056; G06T 2207/30104; G06T 2207/30201; G06T 7/0012; G06T 7/11; G06V 10/25; G06V 10/443; G06V 2201/03; G06V 40/171; G16H 30/40; G16H 40/63; G16H 50/30

See application file for complete search history.

(56) References Cited

U.S. PATENT DOCUMENTS

| | | | |
|---|---|---|---|
| 2009/0105588 A1* | 4/2009 | Emelianov | A61B 5/4869 606/27 |
| 2011/0135771 A1* | 6/2011 | Dubey | A61K 36/328 424/769 |
| 2012/0035540 A1* | 2/2012 | Ferren | A61B 5/076 604/95.01 |
| 2014/0276090 A1* | 9/2014 | Breed | A61B 5/1455 600/473 |
| 2014/0303608 A1* | 10/2014 | Taghizadeh | A61F 7/00 606/20 |
| 2015/0118698 A1* | 4/2015 | Michaelsen | G01N 33/6878 435/7.1 |
| 2015/0196200 A1* | 7/2015 | Fixler | B82Y 15/00 600/431 |
| 2016/0007865 A1* | 1/2016 | Sakata | A61B 5/6898 600/480 |
| 2016/0157725 A1* | 6/2016 | Munoz | A61B 5/0082 600/407 |
| 2017/0209083 A1* | 7/2017 | Zarandi | A61B 5/0816 |
| 2018/0088041 A1* | 3/2018 | Zhang | G01J 5/22 |
| 2018/0098748 A1* | 4/2018 | Kim | A61B 8/0858 |
| 2018/0099001 A1* | 4/2018 | Schentag | G01N 33/6893 |
| 2020/0375451 A1* | 12/2020 | Zavislan | A61B 3/102 |

OTHER PUBLICATIONS

M Anburajan, "Changes of Skin Temperature of Parts of the Body and Serum Asymmetric Dimethylarginine (ADMA) in Type-2 Diabetes Mellitus Indian Patients," Aug. 30-Sep. 3, 2011, 33rd Annual International Conference of the IEEE EMBS, Boston, Massachusetts USA, Aug. 30-Sep. 3, 2011, pp. 6254-6259.*

* cited by examiner

NON-INVASIVE NON-CONTACT SYSTEM AND METHOD FOR MEASURING DYSLIPIDEMIA CONDITION USING THERMAL IMAGING

CROSS REFERENCE TO RELATED APPLICATIONS

This application claims priority to International Patent Application No. PCT/IB2020/059836, filed on Oct. 20, 2020, which claims priority to Indian Patent Application No. 201941044162, filed on Oct. 31, 2019. The contents of these applications are hereby incorporated by reference in their entirety.

TECHNICAL FIELD

The present disclosure generally relates to the technical field of health care systems for evaluating health conditions of a person. More particularly, the present disclosure relates to a non-contact, non-invasive system and method for evaluating dyslipidemia condition of a person by measuring biomarkers associated with atherosclerotic complications and abnormal levels of lipids or lipoproteins using thermal imaging.

BACKGROUND

The background description includes information that may be useful in understanding the present invention. It is not an admission that any of the information provided herein is prior art or relevant to the presently claimed invention, or that any publication explicitly or implicitly referenced is prior art.

Dyslipidemia is a metabolic disorder characterized by an abnormal amount of lipids or lipoproteins in the blood. Blood lipids such as Triglycerides and Cholesterol are fatty substances. Plasma lipoprotein includes high density lipoprotein (HDL), low density lipoprotein (LDL), very low density lipoprotein (VLDL) and chylomicrons. Abnormalities in concentration of the lipids or plasma lipoproteins have been established as a most important risk factor for atherosclerosis. Dyslipidemia condition, once diagnosed, can be managed however it can still cause complications and stimulates risk of long-term damage. Dyslipidemia typically does not have any symptoms hence can remain undetected for a long time until complications are diagnosed. Severe complications of dyslipidemia include coronary artery disease (CAD), peripheral artery disease (PAD), cardiovascular and cerebrovascular diseases (CVDs).

Dyslipidemia can primarily result from genetic factors that can lead to excessive or insufficient production of the lipoproteins. Other causes of the dyslipidemia include lifestyle factors such as dietary habits, consumption of saturated and trans fats, level of physical activity, diabetes mellitus, hypothyroidism, alcohol overuse and others. Based on the concentration of the lipids and lipoproteins, dyslipidemia is classified as hyperlipidemia, hypercholesterolemia, hypertriglyceridemia, hypolipidemia, hyperlipoproteinemia, and hypolipoproteinemia. Hyperlipidemia is the most prevalent and is associated with elevated levels of any or all lipids or lipoproteins. Hypercholesterolemia relates to elevated levels of cholesterol in the blood whereas hypertriglyceridemia is related to elevated levels of triglycerides. Hyperlipoproteinemia relates to elevated levels of lipoproteins in general but more specifically to elevated level of LDLs in the blood. Dyslipidemia in lower intensity, may not be detected for many years until the untreated condition becomes severe and causes symptomatic vascular or other diseases.

Diagnosis, continuous monitoring and treatment are essential in managing the dyslipidemia condition. Complications associated with the dyslipidemia, such as coronary artery disease (CAD), peripheral artery disease (PAD) and atherosclerotic diseases can be prevented or delayed with continuous monitoring and appropriate treatment plan. The clinical diagnosis of dyslipidemia involves measurement of the lipid profile (total cholesterol, LDL, HDL, Triglycerides, VLDL) in the blood serum. A higher level of any or all of total cholesterol, LDL and triglycerides in the blood serum confirms dyslipidemia condition in a person. For an adult, the total cholesterol below 200 mg/dL, LDL below 100 mg/dL, triglycerides below 150 mg/dL and HDL above 30 mg/dL is considered normal. Dyslipidemia is diagnosed if any of the lipid components measured from the blood serum are above their respective specified limits. The lipid profile is typically measured in a clinical facility by drawing blood samples from a vein in an arm and processing the blood serum, causing pain and discomfort.

Among dyslipidemia patients, home-based cholesterol test kits are often preferred by patients to monitor blood lipid levels at home. However, most of these monitors involve invasive techniques such as obtaining blood from a finger prick, causing pain and discomfort, which often results in poor adherence to self-monitoring. Also, these home test kits measure only a total cholesterol level which may not always be accurate and/or sufficient to determine the dyslipidemia condition. Hence, these methods are not preferred for continuous monitoring or multiple pre-screenings. A significant reason is that no simple and unambiguous laboratory test exist that can be used to identify those subjects having dyslipidemia or to identify early signs of onset of the dyslipidemia conditions.

There is, therefore, a need to provide a simple and efficient solution to identify subjects with dyslipidemia conditions so that they can obtain treatment early, and can also monitor progression of the disease over time.

OBJECTS OF THE INVENTION

A general object of the present disclosure is to provide a simple and efficient solution which can obviate the foregoing limitations in the art.

An object of the present disclosure is to provide an improved system for evaluating dyslipidemia conditions of an individual.

Another object of the present disclosure is to provide an efficient system to identify individuals with either having dyslipidemia or showing early signs of dyslipidemia conditions so that they can obtain treatment early, and can also monitor progression of the disease over time.

Another object of the present disclosure is to provide a non-contact, non-invasive system and method for determining dyslipidemia conditions of a person by measuring vascular health using thermal imaging.

Yet another object of the present disclosure is to provide an efficient system and method to use biomarkers associated with atherosclerotic and various hemodynamic factors determined from thermal imaging for measuring dyslipidemia conditions of individuals to help in diagnosis of health conditions.

Still another object of the present disclosure is to provide a simple and cost-effective system and method which can be easily implemented for measuring dyslipidemia conditions of a person.

SUMMARY

Aspects of the present disclosure relate to a non-contact, non-invasive system and method for evaluating dyslipidemia condition in a person. The proposed system and method may be used for provisional diagnosis of dyslipidemia conditions of a patient and for regulating the medications or treatment suitable to the patient over time. This system and method may also be used for early detection of biomarkers indicating risk of developing dyslipidemia conditions, and can use biomarkers associated with atherosclerotic complications and hemodynamic imbalances measured by thermal imaging for assessing the dyslipidemia complications.

Dyslipidemia in a person creates vascular complications over time, such as atherosclerosis. These complications impairs vascular structure, and abnormal levels of lipids and lipoproteins causes hemodynamic imbalances in the person body. These imbalances can be seen in major arteries such as carotid and are used as potential biomarkers to determine dyslipidemia conditions. The blood flow through the arteries emits heat due to peripheral resistance of the arterial wall and is measured using sensitive thermal sensors. Atherosclerotic lesions in the arteries and elevated levels of cholesterol and other lipoproteins create more resistance for the flow of blood and change the hemodynamics. The resistance created from the lesions for the blood flow varies temperature observed along the arterial regions. Extremely low level of the lipids or lipoprotein may also vary the temperature observed due to the change in blood viscosity. This correlation between the blood flow and the temperature variation observed in the arterial region is used as a principle behind this method to measure parameters associated with hemodynamics. The differences in the measured parameters serve as biomarkers for abnormal levels of some or all lipids and lipoproteins.

In an aspect, the disclosed system and method for evaluating dyslipidemia conditions of a subject, such as a human, are based on capturing any or a combination of one or more thermal images and videos of at least one body part, for example an anterior face, of the subject by a set of thermal sensor; and receiving a set of data packets associated with the captured any or a combination of one or more images and videos by a processing engine. The processing engine comprises processors coupled to a memory storing a set of instructions executable by one or more processors to detect a predefined region, for example a face, of the body part in each frame of the captured images and/or videos, and segment one or more portions, a forehead of the subject, from the detected predefined region in each frame of the captured images and/or videos. A region of interest comprising arteries in the segmented portions in each frame of the captured images and/or videos is automatically identified by the processors to extract one or more pixel values, representing a set of biosignals, from each frame of the captured images and/or videos based on the identified region of interest.

In an embodiment, one or more parameters are associated with a rate of atherosclerotic, levels of lipids and lipoproteins, and hemodynamic factors of the subject are determined based on the extracted one or more pixel values to measure a risk score for the dyslipidemia conditions of the subject based on the determined parameters using computational models. Thus, it would be appreciated that the risk score for the dyslipidemia conditions is determined non-invasively without contacting the subject and does not involve any harmful radiation.

In an embodiment, the determined one or more parameters associated with the rate of atherosclerotic, levels of lipids and lipoproteins, and hemodynamic factors correspond to time and frequency domain parameters including, but not limited to, average intensity, signal amplitude, signal period, signal entropy, signal power spectral density, histogram and peak count.

In an exemplary embodiment, the disclosed system and method can be used for various applications, for example provisional diagnosis of the dyslipidemia conditions, regulate medications and treatment suitable to a dyslipidemic patient over time, early detection of biomarkers indicating onset of the dyslipidemia conditions, determine efficacy of lifestyle and medical interventions.

Various objects, features, aspects and advantages of the inventive subject matter will become apparent from the following detailed description of preferred embodiments, along with the accompanying drawing figures in which like numerals represent like components.

BRIEF DESCRIPTION OF THE DRAWINGS

In the figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION

Figure 1:
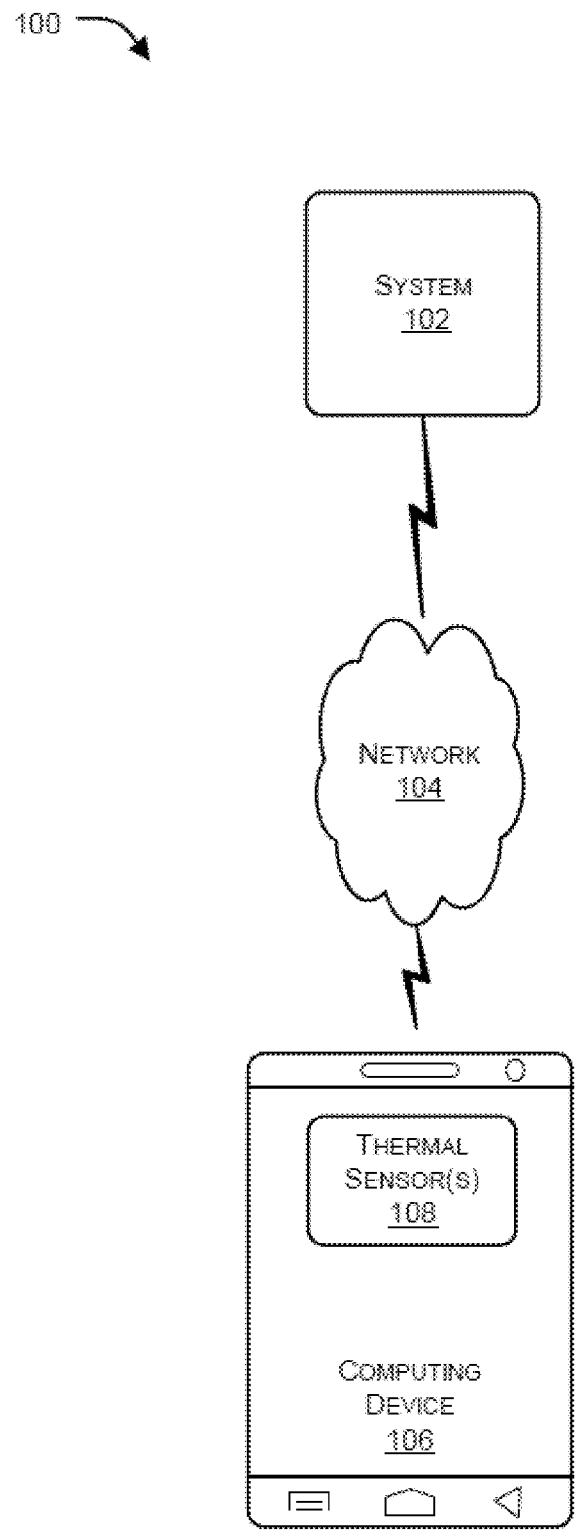
FIG. 1 illustrates an exemplary overall architecture in which or with which the proposed system can be implemented, in accordance with an embodiment of the present disclosure.

The following is a detailed description of embodiments of the disclosure depicted in the accompanying drawings. The embodiments are in such detail as to communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

If the specification states a component or feature "may", "can", "could", or "might" be included or have a characteristic, that particular component or feature is not required to be included or have the characteristic. As used in the description herein and throughout the claims that follow, the meaning of "a," "an," and "the" include plural reference unless the context clearly dictates otherwise. Also, as used in the description herein, the meaning of "in" includes "in" and "on" unless the context clearly dictates otherwise.

Various methods described herein may be practiced by combining one or more machine-readable storage media containing the code according to the present invention with appropriate standard computer hardware to execute the code contained therein. An apparatus for practicing various embodiments of the present invention may involve one or more computers (or one or more processors within the single computer) and storage systems containing or having network access to a computer program(s) coded in accordance with various methods described herein, and the method steps of the invention could be accomplished by modules, routines, subroutines, or subparts of a computer program product.

While embodiments of the present invention have been illustrated and described, it is apparent that the invention is not limited to these embodiments only. Numerous modifications, changes, variations, substitutions, and equivalents will be apparent to those skilled in the art, without departing from the spirit and scope of the invention, as described in the claim.

Embodiments explained herein relate to health care systems for evaluating the health condition of an individual/patient. In particular, the present disclosure relates to a non-contact, non-invasive system and method for measuring dyslipidemia conditions of a person using thermal imaging.

In an aspect, the present disclosure provides a system and method for measuring dyslipidemia conditions of a person. The system and method includes a set of thermal sensors for capturing one or more thermal images or thermal videos of at least one part of a subject body; and a processing engine operatively coupled to the set of thermal sensors, the processing engine comprising a processor coupled to a memory, the memory storing instructions executed by the processor to: pre-process the thermal images and/or videos received from the thermal sensors; for each image from the set of captured thermal images or from the captured thermal videos, define a region of interest (ROI) in each of the image frames; segment the ROI in each of the image frames into a plurality of segments based on thermal gradient pattern; determine the change in thermal gradient values of each pixel in the ROI for a predefined time period to obtain set of time domain values for quantitative analysis and signal processing; determine one or more parameters associated to a rate of atherosclerotic, levels of lipids and lipoproteins, and hemodynamic factors; and compare the determined parameters with a set of predetermined or predefined parameters values observed for healthy subjects, to determine the existence and/or degree of dyslipidemia in the subject/person using computational models.

In another aspect, the system and method for measuring dyslipidemia conditions uses passive thermal videos/images of an anterior face of a subject to measure vascular function and analyze the blood transmission pattern. The frontal branches of major arteries on the forehead, is considered to measure biomarkers of vascular dysfunction. The frontal branch of the arteries typically lay close to a skin surface in the forehead region, and heat intensity can be measured from the thermal image/video captured using an infrared thermal camera. The region related to the arterial structure in the forehead is automatically segmented from each frame of the video/images. The segmented region is further processed to extract the pixel values representing the distribution of temperature or the heat intensity along the arterial section. Time domain values are evaluated using statistical analysis and signal processing techniques to calculate parameters associated with a rate of atherosclerotic, levels of lipids and lipoproteins, and hemodynamic factors of the subject based on the extracted one or more pixel values representing the set of biosignals.

These parameters represent hemodynamics such as, but not limited to, blood flow velocity, pulse rate, blood density and blood pressure. The variations in the thermal intensity along the segmented region represent the occlusions of the arteries due to atherosclerotic lesions. By relating variations in the intensity of heat and the measured parameters with the age of the subject and by comparison with corresponding measurements initially determined from non-dyslipidemic subjects of comparable age, the presence of dyslipidemia can be determined. Moreover, imbalances in the hemodynamic parameters in the ROI are observed in dyslipidemia patients. These factors and their magnitude are considered to measure severity of the dyslipidemia conditions of the subject.

In an embodiment, the disclosed system and methods can be used to identify efficacy of therapeutic interventions, such as to manage dosage overtime of anti-dyslipidemic medication, or to assess success of lifestyle interventions or other treatments to modify disease progression.

FIG. 1 illustrates an exemplary overall architecture in which or with which the proposed system can be implemented, in accordance with an embodiment of the present disclosure.

In an embodiment, an overall architecture 100 includes a system 102 that can be implemented in any computing device that can be configured/operatively coupled with a server. The system 102 can be implemented using any or a combination of hardware components and/or software components such as a server, a computing system, a computing device, a security device and the like, such that embodiments of the present disclosure can measure dyslipidemia conditions for a person. The system 102 can include processors and memory storing instructions executable by the processors. Further, the system 102 can be communicatively coupled with a computing device 106 through a network 104. The computing device 106 can be integrated with a set of thermal sensors 108. The set of thermal sensors 108 can be any or a combination of, but not limited to, a digital camera, a digital single-lens reflex (DSLR) camera, or a standalone infrared camera, a thermal camera, or a monochromatic camera. Those skilled in the art would appreciate that the thermal image can be captured using a thermal camera, the thermal camera senses thermal or infrared radiation emitted from the body of the person and can render images representing the spatial intensity of radiation. Since the images can be captured from an optimal distance, therefore this technique is non-invasive and non-contact.

The network 104 can be a wireless network, a wired network or a combination thereof that can be implemented as one of the different types of networks, such as Intranet, Local Area Network (LAN), Wide Area Network (WAN), Internet, and the like. Further, the network 104 can either be a dedicated network or a shared network. The shared network can represent an association of the different types of networks that can use a variety of protocols, for example, Hypertext Transfer Protocol (HTTP), Transmission Control Protocol/Internet Protocol (TCP/IP), Wireless Application Protocol (WAP), and the like.

Examples of the computing devices 106 can include, but are not limited to, a portable computer, a personal digital assistant, a handheld device, and a workstation. In an embodiment, the computing device 106 is a mobile phone having the imaging device 108. In another embodiment, the imaging device 108 is operatively coupled with the computing device 106. In an embodiment, system 102 facilitates a non-invasive and non-contact technique for determining biomarkers to help determine the dyslipidemia conditions of the person.

In an embodiment, the thermal sensor 108 can be used for capturing thermal images or thermal videos of at least a body part, for example anterior face, of the person. For example, a length of the captured thermal video may range from thirty seconds to one minute. According to an embodiment, during pre-processing the system 102 can receive a set of data packets associated with the captured one or more thermal images and/or the captured thermal videos from the sensors 108 and process set of frames in the captured thermal videos and/or the captured one or more thermal images. The system 102 can detect and extract a predefined region, for example a face, of the subject in each frame of the captured images and/or videos, and segment one or more portions from the detected predefined region in each frame of the captured images and/or videos.

In another embodiment, the system 102 can identify a region of interest comprising arteries in the one or more segmented portions in each frame of the captured images and/or videos, and extract one or more pixel values, representing a set of biosignals, from each frame of the captured images and/or videos based on the identified region of interest. The system 102 can further determine one or more parameters associated with a rate of atherosclerotic, levels of lipids and lipoproteins, and hemodynamic factors of the subject based on the extracted one or more pixel values representing the set of biosignals, and measure a risk score for the dyslipidemia condition based on the determined one or more parameters using computational models. The determined one or more parameters can be associated with potential biomarkers of atherosclerotic complications and hemodynamic imbalances caused due to abnormal levels of some or all of the lipids and lipoproteins. Further, the system 102 may compare the determined one or more parameters associated with the rate of atherosclerotic, levels of lipids and lipoproteins, and hemodynamic factors with predetermined reference parameters to evaluate the dyslipidemia conditions of the subject based on the deviation of the determined one or more parameters with respect to the predetermined reference parameters. Measurement of the risk score for the dyslipidemia condition may also be based on the comparison.

The determined one or more parameters associated with the rate of atherosclerotic, levels of lipids and lipoproteins, and hemodynamic factors can correspond to time and frequency domain parameters which can be any or a combination of average intensity, signal amplitude, signal period, signal entropy, signal power spectral density, histogram and peak count.

In an embodiment, the measurement of the risk score for the dyslipidemia condition or evaluation of the dyslipidemia conditions of the subject may consider the demographics and medical history of the subject along with the determined parameters for evaluating the complications associated with abnormal levels of lipids and lipoproteins.

In an embodiment, the identified region of interest can be associated with the forehead region of the subject comprising frontal branches of the major arteries which lay close to a skin surface on the forehead. The processors can segment the identified region of interest from each of the captured images and/or videos based on difference between thermal intensity along the blood vessel and the thermal intensity in other regions of the forehead. In an exemplary embodiment, the identified region of interest can be segmented using any or a combination of morphological operations, otsu thresholding, edge detection and contour approximations techniques.

In an embodiment, the system 102 can execute a first set of instructions associated with image filtering and enhancing techniques on each of the captured any or a combination of the images and videos for removing noise and improving quality.

In an embodiment, the predefined region such as the facial region in each frame of the captured images and/or videos can be detected based on execution of a second set of instruction associated with image processing including face detection and landmark detection.

In an embodiment, the system 102 can perform spatial transformation on the identified region of interest to obtain a quantitative representation of a pattern observed in each frame of the captured any or a combination of the one or more images and videos, representing a set of bio signals waveform, along an arterial section associated with pulsatile nature of blood flow.

In an embodiment, the system 102 can be configured to normalize and filter the one or more extracted pixel values representing the set of bio signals to determine time domain values by applying statistical analysis on the filtered pixel values.

In an exemplary embodiment, the system 102 can determine frequency domain values by applying Fast Fourier Transform and frequency filtering technique on the determined time domain values.

In an embodiment, the system 102 can determine, using signal processing techniques, signal parameters comprising the time and frequency domain parameters based on the determined frequency domain values and time domain values.

In an embodiment, the determined time and frequency domain parameters can be associated with any or a combination of the hemodynamics factors, rate of atherosclerotic, levels of lipids and lipoproteins, general healthiness of the artery itself or physiological data indicating core temperature, blood flow velocity, blood density, arterial stiffness, and oxygen saturation in blood.

Figure 2:
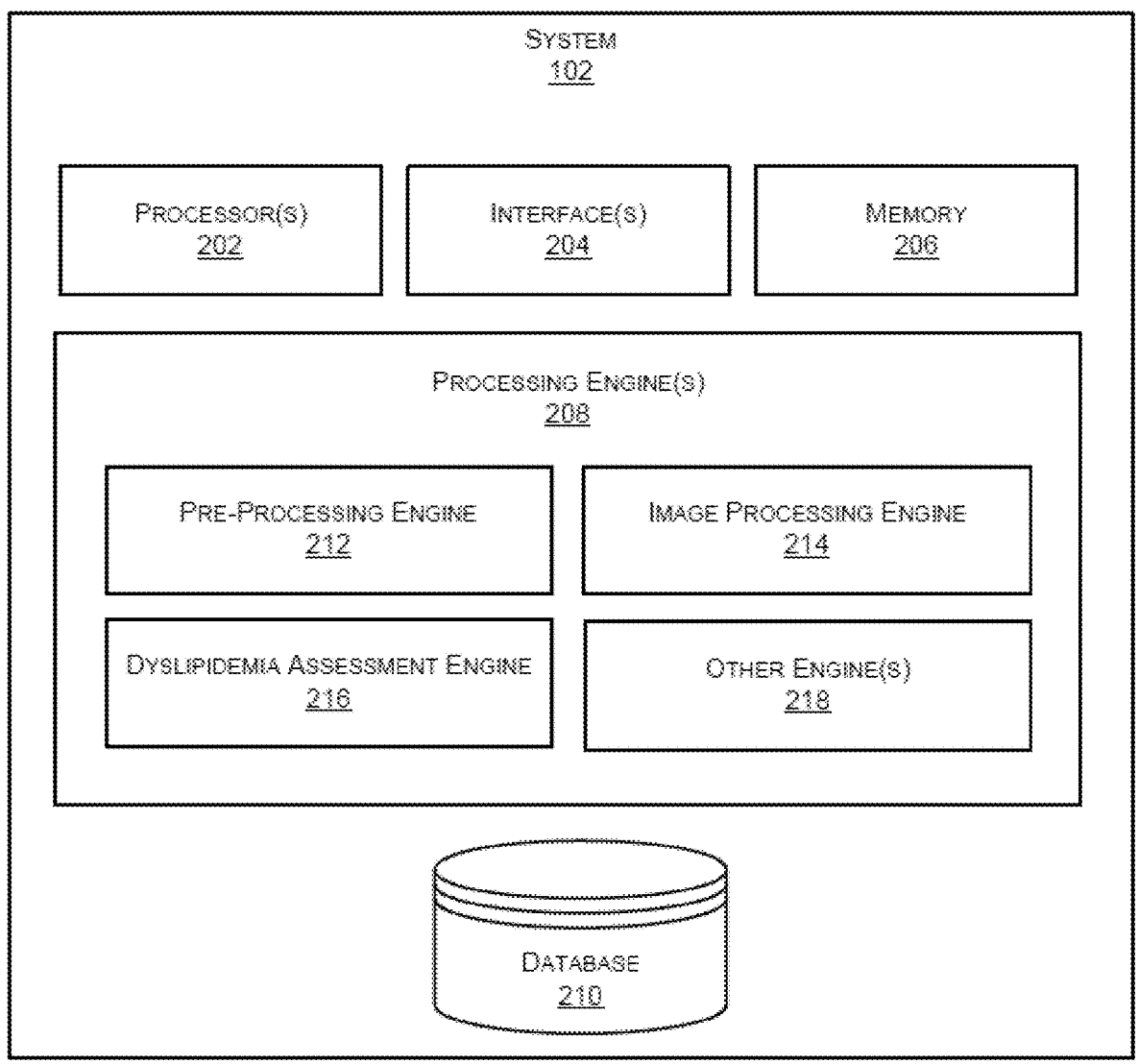
FIG. 2 illustrates exemplary functional components of the proposed system, in accordance with an embodiment of the present disclosure.

FIG. 2 illustrates exemplary functional components of the proposed system, in accordance with an embodiment of the present disclosure.

In an aspect, the system 102 may comprise one or more processor(s) 202. The one or more processor(s) 202 may be implemented as one or more microprocessors, microcomputers, microcontrollers, digital signal processors, central processing units, logic circuitries, and/or any device that manipulates data based on operational instructions. Among other capabilities, the one or more processor(s) 202 are configured to fetch and execute computer-readable instructions stored in a memory 206 of the system 102. The memory 206 may store one or more computer-readable instructions or routines, which may be fetched and executed to create or share the data units over a network service. The memory 206 may comprise any non-transitory storage device including, for example, volatile memory such as RAM, or non-volatile memory such as EPROM, flash memory, and the like.

The system 102 may also comprise an interface(s) 204. The interface(s) 204 may comprise a variety of interfaces, for example, interfaces for data input and output devices, referred to as I/O devices, storage devices, and the like. The interface(s) 204 may facilitate communication of system 102 with various devices coupled to the system 102 such as input and output units. The interface(s) 204 may also provide a communication pathway for one or more components of the system 102. Examples of such components include, but are not limited to, processing engine(s) 208 and a data/database 210.

The processing engine(s) 208 may be implemented as a combination of hardware and programming (for example, programmable instructions) to implement one or more functionalities of the processing engine(s) 208. In examples described herein, such combinations of hardware and programming may be implemented in several different ways. For example, the programming for the processing engine(s) 208 may be processor-executable instructions stored on a non-transitory machine-readable storage medium and the hardware for the processing engine(s) 208 may comprise a processing resource (for example, one or more processors), to execute such instructions. In the present examples, the machine-readable storage medium may store instructions that, when executed by the processing resource, implement the processing engine(s) 208. In such examples, the system 102 may comprise the machine-readable storage medium storing the instructions and the processing resource to execute the instructions, or the machine-readable storage medium may be separate but accessible to system 102 and the processing resource. In other examples, the processing engine(s) 208 may be implemented by electronic circuitry.

The database 210 may comprise data that can be either stored or generated as a result of functionalities implemented by any of the components of the processing engine(s) 208. The database 210 may store a set of instructions, for example a first set of instructions, a second set of instructions and/or other required predetermined parameters data/instructions/algorithms to be used by the processors/processing engine 208.

In an exemplary embodiment, the processing engine(s) 208 may comprise a pre-processing engine 212, an image processing engine 214, a dyslipidemia assessment engine 216 and other engines (s) 218.

It would be appreciated that modules being described are only exemplary modules, and any other module or submodule may be included as part of the system 102. These modules too may be merged or divided into super-modules or sub-modules as may be configured.

Pre-Processing Engine 212

Figure 4A:
FIG. 4A illustrates a sequence of frames from captured thermal video/images using an infrared thermal camera, in accordance with an embodiment of the present disclosure.
Figure 4B:
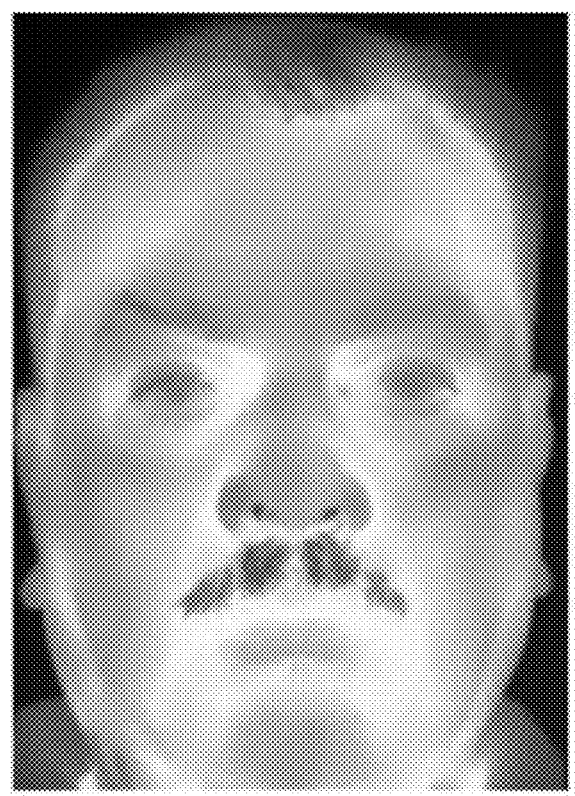
FIG. 4B illustrates a segment of a facial region detected using face detection techniques and extracted from captured thermal images, in accordance with an embodiment of the present disclosure.

In an aspect, the pre-processing engine 212 receives a sequence of thermal image/video frames from the thermal sensors 108 of the computing device 106. FIG. 4A depicts a sequence of thermal image frames including an anterior face obtained from the thermal sensors. The received thermal image/video frames may be converted into grayscale for processing. Further, the pre-processing engine 212 applies image filtering and enhancement techniques on the received frames to remove noise and ensure quality of the thermal images is sufficient before processing. The pre-processing engine 212 then uses a face detection model such as a haar cascade classifier on each of the frames in order to detect a predefined region, such as a facial region, on the frame as shown in FIG. 4B. The pre-processing engine 212 can reject the captured thermal video when no face is detected. Further, the pre-processing engine 212 also uses tracking methods to detect and extract the facial region in subsequent frames to ensure a uniform set of frame segments.

In an embodiment, in order to ensure faster processing, the pre-processing engine 212 may perform contrast stretching, which is efficient as well as a computationally cheap technique implemented to enhance image quality. Those skilled in the art would appreciate that the pre-processing engine 212 focuses on enhancement and performs certain operations on the input image frames to ensure that processing in subsequent stages through the implementation of various other engines can be performed in less computational time. The enhancement of image frames can further be optimized to stay free from floating-point operations.

Image Processing Engine 214

Figure 4C:
FIG. 4C illustrates a forehead region segmented from a face to identify a region of interest comprising arteries, in accordance with an embodiment of the present disclosure.

In an embodiment, the image processing engine 214 receives pre-processed frames of the thermal images/videos including the face region segmented in the frames. The image processing engine 214 may use facial landmark detection algorithms on the set of preprocessed frames to determine the position of eyes or eyebrows in the facial region of the frames. The position of the eyes obtained is further used to segment one or more portions such as forehead region from the set of the preprocessed frames as shown in FIG. 4C. In another embodiment, the image processing engine 214 may further define a region of interest (ROI) for each image frame from the set of image frames received from the pre-processing engine 212. The defined region of interest includes various branches of major arteries in the forehead, which is segmented based on heat distribution on the forehead. The image processing engine 214 may use a bilateral 2D filter on the segmented forehead region in each of the preprocessed frames to remove noise while preserving the edge due to the thermal intensity gradient. Further, since the forehead region comprising the blood vessel is brighter than the surrounding region of the forehead due to heat emitted during blood flow, the region of interest in each of the frames is segmented using a combination of morphological operations such as erosion and opening operation followed by Otsu thresholding, edge detection and contour approximations. The segments extracted from each of the set of frames resemble a vascular structure correlating to the arterial section.

Image segmentation is the process of partitioning a digital image into multiple regions or sets of pixels. Mostly, image partitions are different objects which have the same texture or color. The image segmentation results are a set of regions that cover the entire image together and a set of contours extracted from the image. All of the pixels in a region are similar with respect to some characteristics such as color, intensity, or texture. Adjacent regions are considerably different with respect to the same individuality. The different approaches include but are not limited to (i) by finding boundaries between regions based on discontinuities in intensity levels, (ii) thresholds based on the distribution of pixel properties, such as intensity values, and (iii) based on finding the regions directly. Thus, the choice of an image segmentation technique is depending on the problem being considered.

Region-based methods are based on continuity. These techniques divide the entire image into sub-regions depending on some rules like all the pixels in one region must have the same grey level. Region-based techniques rely on common patterns in intensity values within a cluster of neighboring pixels. The cluster is referred to as the region in addition to group the regions according to their anatomical or functional roles are the goal of the image segmentation. A threshold is the simplest way of segmentation. Using thresholding technique regions can be classified on the basis of range values, which is applied to the intensity values of the image pixels. Thresholding is the transformation of an input image to an output that is a segmented binary image-segmentation methods based on finding the regions for abrupt changes in the intensity value.

When images are processed for enhancement, and while performing some operations like thresholding, more is the chance for distortion of the image due to noise. As a result, imperfections exist in the structure of the image. The primary goal of the morphological operation is to remove this imperfection that mainly affects the shape and texture of images. It is evident that morphological operations can be instrumental in image segmentation as the process directly deals with 'shape extraction' in an image. Morphology in the context of image processing means the description of the shape and structure of the object in an image. Morphological operations work on the basis of set theory and rely more on the relative ordering of the pixel instead of the numerical value. This characteristic makes them more useful for image processing. Those skilled in the art would appreciate the significance of these techniques in image segmentation.

Figure 4D:
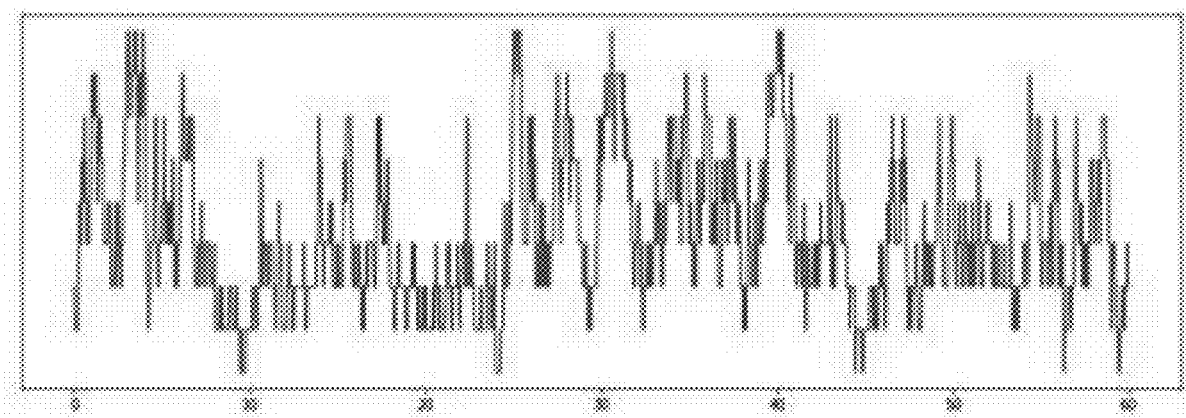
FIG. 4D illustrates an exemplary biosignal waveform determined from pixel values extracted from a region of interest, in accordance with an embodiment of the present disclosure.

In an embodiment, the image processing engine 214 uses the segmented regions to extract pixel values, representing a set of biosignals, from each of the frames for describing changes in the temperature over time. The change in these pixel values correlates with transmission of the blood through the arterial cross-section. The pixel values in the region of interest are spatially transformed to obtain a quantitative representation of a pattern observed in each frame. The spatial transformation includes applying block-based averaging functions and determining the maximum pixel intensity values along the cross-sectional axis. The values can be represented as a series—

$$X(t)_1^T = \text{Max}_{i=0, j=0}^{i+B_w <= w, j+B_h <= h} \left[ \left( \sum_{x=i}^{B_w} \sum_{y=j}^{B_h} P(x, y) \right) / (B_w * B_h) \right]$$

where X(t) is the time domain value for the frame t, P(x,y) is the pixel intensity at position (x,y), $B_w$, $B_h$ is the width and height of the block. The extracted pixel values are represented as a set of one or more time domain biosignals which are then used by other modules/engines to evaluate and measure atherosclerotic complications and/or hemodynamic imbalances caused by the abnormal levels of lipids or lipoproteins. FIG. 4D illustrates an exemplary biosignal waveform extracted from the region of interest of an individual.

Dyslipidemia Assessment Engine 216

In an embodiment, the dyslipidemia assessment engine 216 is used for evaluating the dyslipidemia conditions by determining and comparing parameters pertaining to a rate of atherosclerotic, levels of lipids and lipoproteins, and hemodynamic factors. The pixel values representing the set of biosignals extracted from the image processing engine 214 are initially normalized using min-max normalization. The normalized time data is then transformed to obtain time or frequency domain data using the function, P(X)

$$\omega(k)_0^T = F_{f=0.67}^{1.67} \left[ \sum_{n=0}^{N} X[n] e^{(-2\pi i k n)/N} \right]$$

where the dyslipidemia assessment engine 216 uses Fast Fourier Transform on the data to obtain frequency domain values. The frequency values are then filtered 'F' to select the frequencies in between 0.67 Hz and 1.7 Hz in order to select the signal in the frequency range of the pulse. The assessment engine 216 further applies signal processing techniques on these filtered data to calculate time and frequency domain parameters such as, but not limited to, average intensity, signal amplitude, signal period, signal entropy, signal power spectral density, histogram and peak count for each of the signals obtained independently. The combination of one or more of these parameters is associated with the rate of atherosclerotic, levels of lipids and lipoproteins, and hemodynamic factors. This assessment is subject to thermal pattern analysis and signals analysis on the pulsatile nature of thermal changes in accordance with the pulsatile blood flow.

Figure 5A:
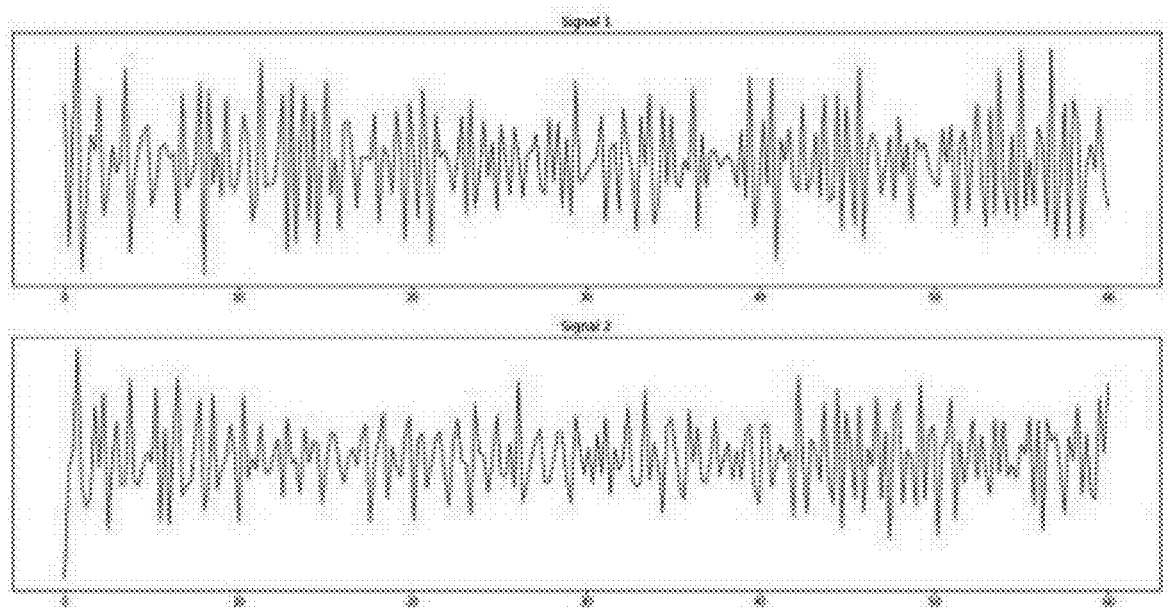
FIG. 5A illustrates two exemplary biosignals obtained and filtered from a region of interest of a healthy person, in accordance with an embodiment of the present disclosure.
Figure 5B:
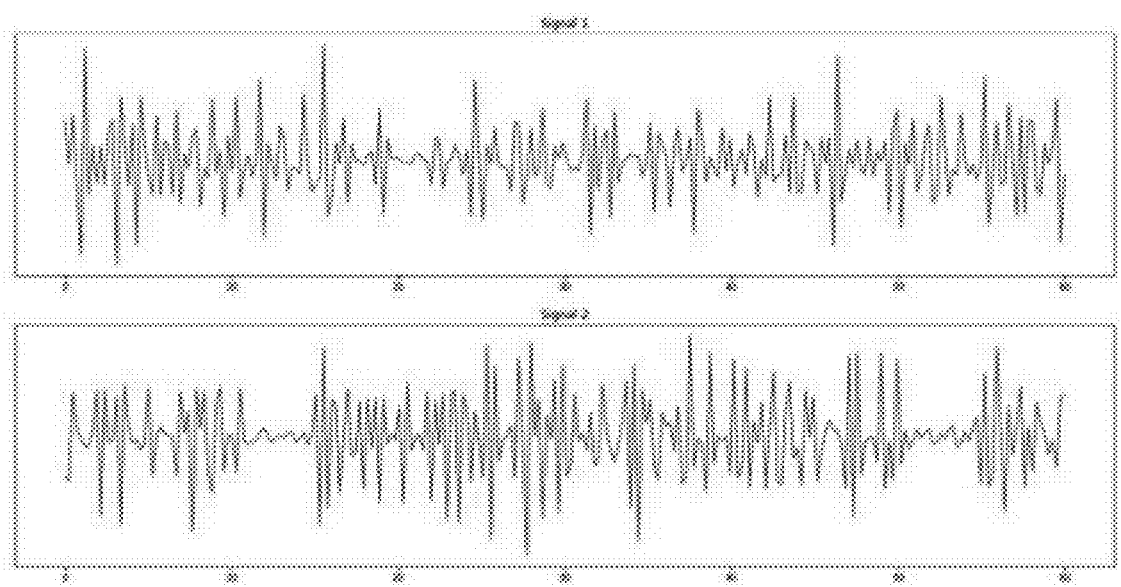
FIG. 5B illustrates two exemplary biosignals obtained and filtered from a region of interest of a dyslipidemic person, in accordance with an embodiment of the present disclosure.

In another embodiment, computation models in the dyslipidemia assessment engine 216 can be initially developed by first calculating the signal parameters for the set of one or more signals extracted from the region of interest of both healthy individuals and patients having dyslipidemia conditions. The assessment engine 216 applies principal component analysis on the calculated signal parameters of the healthy individuals and the dyslipidemia patients to determine the parameters that are most relevant in determining the dyslipidemia condition. The set of selected parameters are further analyzed and compared using statistical methods to identify variations and relative differences between the signals extracted from healthy individuals and dyslipidemia patients. FIG. 5A and FIG. 5B illustrates the set of two filtered signals obtained from a healthy individual and a dyslipidemia patient respectively. As shown, the two signals from the healthy individual in the FIG. 5A are similar while the signals from the dyslipidemia person are different and show temporal variations. The variations define the imbalances associated with atherosclerotic complications and hemodynamic imbalances in the arteries and can be normalized based on age and other physical factors. The set of parameters and the variations identified are then structured as the training data to train the computation models using machine learning units including a set of algorithms for scoring the dyslipidemia conditions of a person. The score obtained using the computation model can be formulated as:

$$S = z/(1+z)$$

where, $z = e^{\sum_{i=1}^{n}(w_i p_i)}$ where $\Sigma w_i p_i$ represents the weighted sum of the set of selected signal parameters.

In an embodiment, the assessment engine 216 uses the computational models on the determined parameters to determine a risk score that relates to the dyslipidemia condition or the atherosclerotic complications and hemodynamic imbalances caused due to abnormal levels of lipids and lipoproteins. The risk score can have a value on a scale like 0-1, 1-10, where the severity increases with the increase in score value. The assessment may also take into consideration demographics and medical history for comparing and calculating the dyslipidemia risk score. The dyslipidemia risk score can be used either to measure the dyslipidemia conditions and/or to evaluate the risk of developing dyslipidemia.

Figure 3:
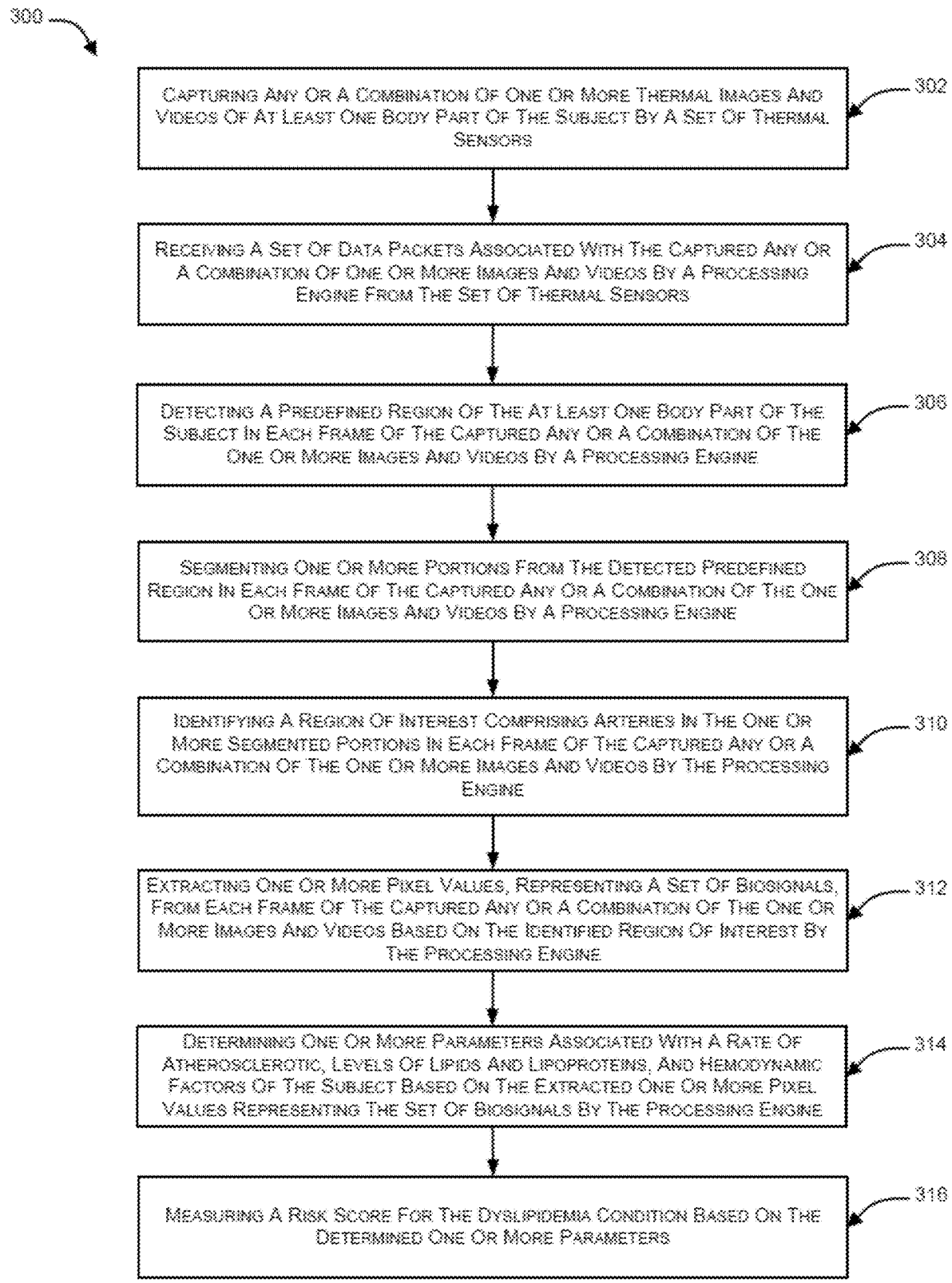
FIG. 3 illustrates a flow diagram illustrating a method for measuring the dyslipidemia condition of a subject, in accordance with an embodiment of the present disclosure.

FIG. 3 illustrates a flow diagram of the proposed method for measuring the dyslipidemia conditions of a person, in accordance with an embodiment of the present disclosure.

In an aspect, the proposed method may be described in the general context of computer-executable instructions. Generally, computer-executable instructions include routines, programs, objects, components, data structures, procedures, modules, functions, etc. that perform particular functions or implement particular abstract data types. The method can also be practiced in a distributed computing environment where functions are performed by remote processing devices that are linked through a communications network. In a distributed computing environment, computer-executable instructions may be located in both local and remote computer storage media, including memory storage devices.

The order in which the method as described is not intended to be construed as a limitation and any number of the described method blocks may be combined in any order to implement the method or alternate methods. Additionally, individual blocks may be deleted from the method without departing from the spirit and scope of the subject matter described herein. Furthermore, the method may be implemented in any suitable hardware, software, firmware, or combination thereof. However, for ease of explanation, in the embodiments described below, the method may be considered to be implemented in the above-described system.

In the context of a flow diagram 300, a block 302 pertains to capturing any or a combination of one or more thermal images and videos of at least one body part, for example anterior face, of the subject by a set of thermal sensors.

Further, a block 304 pertains to receiving a set of data packets associated with the captured any or a combination of one or more images and videos by a processing engine from the set of thermal sensors. The processing engine may perform pre-processing on the thermal images or thermal videos received from the set of thermal sensors for noise reduction and quality enhancement.

Further, a block 306 pertains to detecting a predefined region, for example a facial region, of the subject in each frame of the captured any or a combination of the one or more images and videos by the processing engine on receipt of the set of data packets.

Further, a block 308 pertains to segmenting one or more portions, for example a forehead, from the detected predefined region in each frame of the captured any or a combination of the one or more images and videos by the processing engine, and a block 310 pertains to identifying a region of interest comprising one or more arteries in the one or more segmented segmented/forehead portions in each frame of the captured any or a combination of the one or more images and videos by the processing engine.

Further, a block 312 pertains extracting one or more pixel values, representing a set of biosignals, from each frame of the captured any or a combination of the one or more images and videos based on the identified region of interest by the processing engine, and a block 314 pertains to determining one or more parameters associated with a rate of atherosclerotic, levels of lipids and lipoproteins, and hemodynamic factors of the subject based on the extracted one or more pixel values representing the set of biosignals by the processing engine.

Further, a block 316 pertains to measuring a risk score for the dyslipidemia condition based on the determined one or more parameters. The risk score can be measured using computational models. The determined one or more parameters can be associated with atherosclerotic complications and hemodynamic imbalances and can correspond to the time and frequency domain parameters such as average intensity, signal amplitude, signal period, signal entropy, signal power spectral density, histogram and peak count.

In an embodiment, measurement of the risk score for the dyslipidemia conditions can be based on comparison of the determined parameters associated with the rate of atherosclerotic, levels of lipids and lipoproteins, and hemodynamic factors with the predetermined parameters of healthy and dyslipidemic individuals. The measured risk score relates to the atherosclerotic complications and hemodynamic imbalances caused by abnormal levels of some or all lipids and lipoproteins.

In an embodiment, a process of generating the computational models can include (a) calculating signal parameters for one or more signals associated with the arterial section of both healthy subjects and dyslipidemia patients; (b) identifying a set of parameters that correlate to complications associated with the dyslipidemia condition using a principal component analysis on the calculated signal parameters; (d) determining patterns and differences among the parameters between the dyslipidemia patients and healthy subjects by using statistical methods and visualization; and (e) training the computing models by using machine learning algorithms comprising clustering models, logistic regression, random forest, neural network model on the set of parameters.

Thus, the present disclosure provides a non-invasive, non-contact passive system method for measuring dyslipidemia conditions of an individual using thermal imaging, includes assessing biomarkers pertaining to atherosclerotic complications and hemodynamic imbalances, such as a rate of atherosclerotic, levels of lipids and lipoproteins, and hemodynamic factors of the individual from the thermal image/video. The passive thermal images/videos comprising a front face of the subject are acquired using a thermal infrared camera to auto-detect and segment frontal branches of major arterial regions from a forehead region. The frontal branches of the arteries are segmented based on heat variations on the forehead. Tracking methods are used to segment a region of interest from the forehead in the sequence of captured images and/or videos. Parameters indicating the atherosclerotic complications and hemodynamic factors are calculated from the segmented region of interest by applying thermal pattern analysis and signal analysis on pulsatile nature of thermal changes in accordance with the pulsatile blood flow. The system and method includes analysis of determined parameters to identify imbalances and deviations of the values from predetermined normal/reference range. The state of dyslipidemia condition is measured based on the imbalances in the determined parameters that correlate to the abnormal levels of the lipids and lipoproteins causing vasoconstriction.

Thus, it will be appreciated by those of ordinary skill in the art that the diagrams, schematics, illustrations, and the like represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular name.

While embodiments of the present invention have been illustrated and described, it is apparent that the invention is not limited to these embodiments only. Numerous modifications, changes, variations, substitutions, and equivalents will be apparent to those skilled in the art, without departing from the spirit and scope of the invention, as described in the claim.

In the foregoing description, numerous details are set forth. It is apparent, however, to one of ordinary skill in the art having the benefit of this disclosure, that the present invention may be practiced without these specific details. In some instances, well-known structures and devices are shown in block diagram form, rather than in detail, to avoid obscuring the present invention.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of this document terms "coupled to" and "coupled with" are also used euphemistically to mean "communicatively coupled with" over a network, where two or more devices are able to exchange data with each other over the network, possibly via one or more intermediary devices.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

ADVANTAGES OF THE PRESENT DISCLOSURE

The present disclosure provides a simple and efficient solution which can obviate the foregoing limitations in the art.

The present disclosure provides an improved system for evaluating dyslipidemia conditions of an individual.

The present disclosure provides an efficient system to identify individuals with either having dyslipidemia or showing early signs of dyslipidemia conditions so that they can obtain treatment early, and can also monitor progression of the disease over time.

The present disclosure provides a non-contact, non-invasive system and method for determining dyslipidemia condition of a person by measuring vascular health using thermal imaging.

The present disclosure provides an efficient system and method to use biomarkers associated with atherosclerotic complications and hemodynamic imbalances determined from thermal imaging for measuring dyslipidemia conditions of individuals to help in diagnosis of the health conditions.

The present disclosure provides a simple and cost-effective system and method which can be easily implemented for measuring dyslipidemia conditions of a person.

We claim:

1. A system for measuring dyslipidemia condition of a subject, the system comprising:
    a set of thermal sensors for capturing any or a combination of one or more thermal images and videos of at least one body part of the subject; and
    a processing engine operatively coupled to the set of thermal sensors, and comprising one or more processors coupled to a memory, the memory storing a set of instructions executable by the one or more processors to:
        receive a set of data packets associated with the captured any or a combination of one or more images and videos from the set of thermal sensors;
        detect a predefined region of the at least one body part of the subject in each frame of the captured any or a combination of the one or more images and videos on receipt of the set of data packets;
        segment one or more portions from the detected predefined region in each frame of the captured any or a combination of the one or more images and videos;
        identify a region of interest comprising one or more arteries in the one or more segmented portions in each frame of the captured any or a combination of the one or more images and videos;
        extract one or more pixel values, representing a set of biosignals, from each frame of the captured any or a combination of the one or more images and videos based on the identified region of interest;
        determine one or more parameters associated with a rate of atherosclerotic, levels of lipids and lipoproteins, and hemodynamic factors of the subject based on the extracted one or more pixel values representing the set of biosignals; and
        measure a risk score for the dyslipidemia condition based on the determined one or more parameters.

2. The system as claimed in claim 1, wherein the set of thermal sensors are selected from a group comprising a digital camera, a digital single-lens reflex (DSLR) camera, an infrared thermal camera, and wherein the set of thermal sensors sense heat or infrared radiation emitted from the body past of the subject and renders images and videos representing a spatial intensity of radiation.

3. The system as claimed in claim 1, wherein the determined one or more parameters are associated with potential biomarkers of atherosclerotic complications and hemodynamic imbalances, and wherein measurement of the risk score for the dyslipidemia condition is based on comparison of the determined one or more parameters with predetermined set of reference parameters that are stored in a database operatively coupled to the processing engine.

4. The system as claimed in claim 1, wherein the subject is a human.

5. The system as claimed in claim 1, wherein the at least one body parts of the subject is an anterior face of the subject, and wherein the segment one or more portions are associated with a forehead of the subject.

6. The system as claimed in claim 5, wherein the identified region of interest is associated with a forehead region of the subject comprises frontal branches of the arteries which lay close to a skin surface on the forehead.

7. The system as claimed in claim 6, wherein one or more processors are configured to segment the identified region of interest from each of the captured any or a combination of the one or more images and videos based on difference between thermal intensity along the arteries and thermal intensity in other regions of the forehead.

8. The system as claimed in claim 7, wherein the identified region of interest is segmented using any or a combination of morphological operations, otsu thresholding, edge detection and contour approximations techniques.

9. The system as claimed in claim 1, wherein the one or more processors are configured to execute a first set of instructions associated with image filtering and enhancing techniques on each of the captured any or a combination of the one or more images and videos for removing noise and improving quality.

10. The system as claimed in claim 1, wherein the one or more processors are configured to execute a second set of instructions associated with image processing including face detection and landmark detection to detect the predefined region of the at least one body part in each frame of the captured any or a combination of the one or more images and videos.

11. The system as claimed in claim 1, wherein the one or more processor are configured to perform spatial transformation on the identified region of interest to obtain a quantitative representation of a pattern observed in each frame of the captured any or a combination of the one or more images and videos, representing a set of biosignals waveform along an arterial section associated with pulsatile nature of blood flow.

12. The system as claimed in claim 1, wherein the one or more processors are configured to normalize and filter the one or more extracted pixel values representing the set of biosignals, and wherein the one or more processors are configured to determine time domain values by applying statistical analysis on the filtered pixel values.

13. The system as claimed in claim 12, wherein the one or more processors are configured to determine frequency domain values by applying Fast Fourier Transform and frequency filtering technique on the determined time domain values.

14. The system as claimed in claim 13, wherein the one or more processors are configured to determine, using signal processing techniques, signal parameters comprising time and frequency domain parameters based on the determined frequency domain values and time domain values.

15. The system as claimed in claim 14, wherein the determined time and frequency domain parameters comprises any or a combination of average intensity, signal amplitude, signal period, signal entropy, signal power spectral density, histogram and peak count, and wherein the time and frequency domain parameters are also associated with any or a combination of the hemodynamics factors, rate of atherosclerotic, levels of lipids and lipoproteins, general healthiness of the artery itself or physiological data core temperature, blood flow velocity, blood density, arterial stiffness, and oxygen saturation in blood.

16. The system as claimed in 1, wherein the measurement of the risk score for the dyslipidemia condition of the subject considers demographics and medical history of the subject along with the determined parameters for evaluating the dyslipidemia condition.

17. The system as claimed in claim 1, wherein the determined one or more parameters are associated with a vasoconstriction of the subject.

18. The system as claimed in claim 1, wherein the measurement of the risk score for the dyslipidemia condition is performed using computational modals, and wherein generation of the computational models comprises:
calculating signal parameters for one or more signals associated with the arterial section of both a healthy subject and a dyslipidemia subject;
identifying a set of parameters that correlate to complications associated with the dyslipidemia condition using a principal component analysis on the calculated signal parameters;
determining patterns and differences among the parameters between the dyslipidemia and healthy subjects by using statistical methods and visualization; and
training the computing models by using machine learning units comprising clustering models, logistic regression, random forest, neural network model on the set of parameters.

19. A method for measuring dyslipidemia condition of a subject, the method comprising:
capturing, by a set of thermal sensors, any or a combination of one or more thermal images and videos of at least one body part of the subject;
receiving, by a processing engine, a set of data packets associated with the captured any or a combination of one or more images and videos from the set of thermal sensors operatively coupled to the processing engine;
detecting, by the processing engine, a predefined region of the at least one body part of the subject in each frame of the captured any or a combination of the one or more images and videos on receipt of the set of data packets;
segmenting, by the processing engine, one or more portions from the detected predefined region in each frame of the captured any or a combination of the one or more images and videos;
identifying, by the processing engine, a region of interest comprising arteries in the one or more segmented portions in each frame of the captured any or a combination of the one or more images and videos;
extracting, by the processing engine, one or more pixel values, representing a set of biosignals, from each frame of the captured any or a combination of the one or more images and videos based on the identified region of interest;
determining, by the processing engine, one or more parameters associated with a rate of atherosclerotic, levels of lipids and lipoproteins, and hemodynamic factors of the subject based on the extracted one or more pixel values representing the set of biosignals;
measuring, by the processing engine, a risk score for the dyslipidemia condition based on the determined one or more parameters.

* * * * *